US005620561A

United States Patent [19]
Kuhn et al.

[11] Patent Number: 5,620,561
[45] Date of Patent: Apr. 15, 1997

[54] VORTEX EVAPORATION

[75] Inventors: Lowell L. Kuhn, Independence; James F. Ptacek, Kansas City; Gary P. Roepke, Blue Springs, all of Mo.

[73] Assignee: Labconco Corporation, Kansas City, Mo.

[21] Appl. No.: 444,523

[22] Filed: May 19, 1995

Related U.S. Application Data

[62] Division of Ser. No. 234,241, Apr. 28, 1994, Pat. No. 5,569,357.

[51] Int. Cl.⁶ .................................................. B01D 1/00
[52] U.S. Cl. .......................... 159/47.1; 159/16.1; 159/44; 159/DIG. 16; 203/1; 203/2; 203/49; 203/91
[58] Field of Search .................... 159/16.1, 44, DIG. 16, 159/47.1; 203/49, 1, 2, 91, DIG. 18; 494/25, 82; 366/4–5, 22, 29, 31; 202/160, 175, 206, 238, 205

[56] References Cited

U.S. PATENT DOCUMENTS

| | | | |
|---|---|---|---|
| 3,580,817 | 5/1971 | Schnur | 203/11 |
| 3,654,981 | 4/1972 | Aitchison | 159/6.1 |
| 3,725,209 | 4/1973 | Rosa | 202/238 |
| 3,812,654 | 5/1974 | Brown | 95/223 |
| 3,837,491 | 9/1974 | Hamiston et al. | 202/238 |
| 3,890,205 | 6/1975 | Schnitzer | 203/22 |
| 3,977,935 | 8/1976 | Kowarski | 159/23 |
| 4,280,902 | 7/1981 | Jacobsen et al. | 210/512.1 |
| 4,790,911 | 12/1988 | Parkinson | 159/11.1 |
| 4,938,868 | 7/1990 | Nelson | 202/175 |
| 5,005,981 | 4/1991 | Schulte et al. | 366/219 |
| 5,078,880 | 1/1992 | Barry | 159/16.1 |
| 5,084,133 | 1/1992 | Guy et al. | 159/6.1 |
| 5,100,623 | 3/1992 | Friswell | 422/68.1 |
| 5,176,799 | 1/1993 | Roe et al. | 159/16.1 |
| 5,211,808 | 5/1993 | Vilardi et al. | 159/6.1 |
| 5,217,904 | 6/1993 | Bruno | 157/16.1 |
| 5,221,439 | 6/1993 | Li et al. | 159/13.2 |

OTHER PUBLICATIONS

Turbo Vap LV, Zymark Corporation, Feb. 1991.
Turbo Vap II Concentration Workstation, Zymark Corporation Dec., 1991.
Analytical Evaporators, Extractors and Accessories, Organomation Associates, Inc.
Rotation–Schwingverdampfer, Orbistat, Sep. 1992.

Primary Examiner—Virginia Manoharan
Attorney, Agent, or Firm—Shook, Hardy & Bacon L.L.P.

[57] ABSTRACT

A method of evaporating liquid from a liquid and solid solution in a container within a chamber involves moving the container in an orbital motion such that the solution forms a vortex configuration within the container and also involves directing gas into the container. The gas is directed into the container from a point source above the liquid in the container to decrease the partial pressure on the solution thereby increasing the evaporation rate of the liquid from the solution. To further increase evaporation of the liquid, heat may be applied to the container. The temperature within the chamber may be regulated by sensing the temperature within the chamber and controlling the application of heat to the container in response to the temperature sensed within the chamber. An alternative method of evaporating liquid from a liquid and solid solution in a container within a chamber also involves moving the container in an orbital motion, but further involves drawing a vacuum within the chamber rather than directing gas into the container.

15 Claims, 4 Drawing Sheets

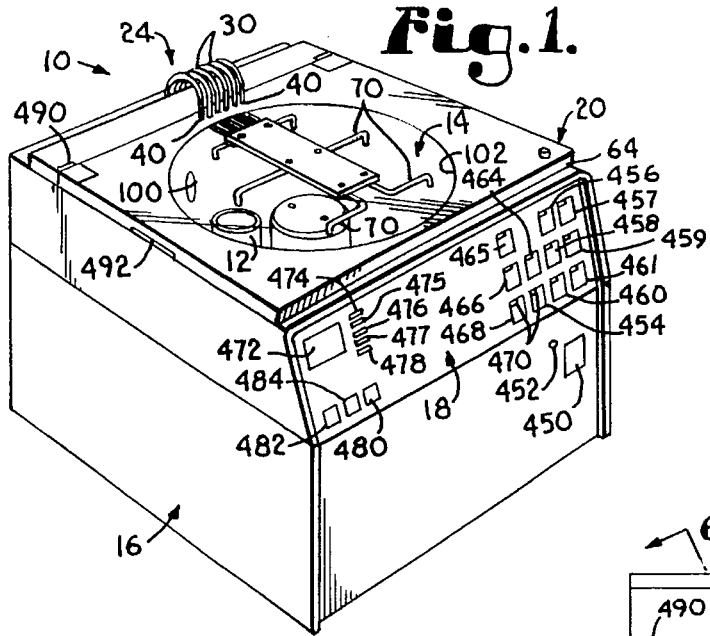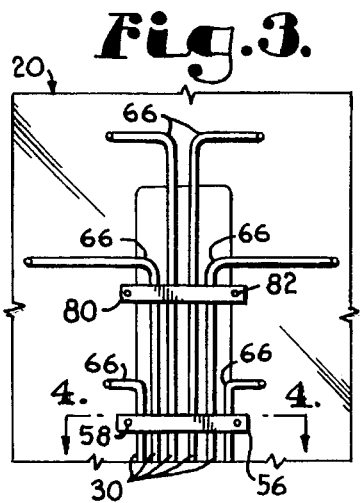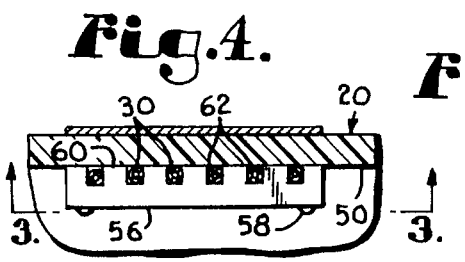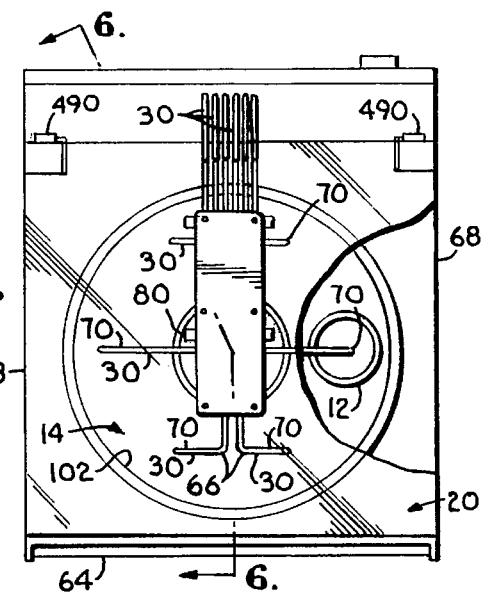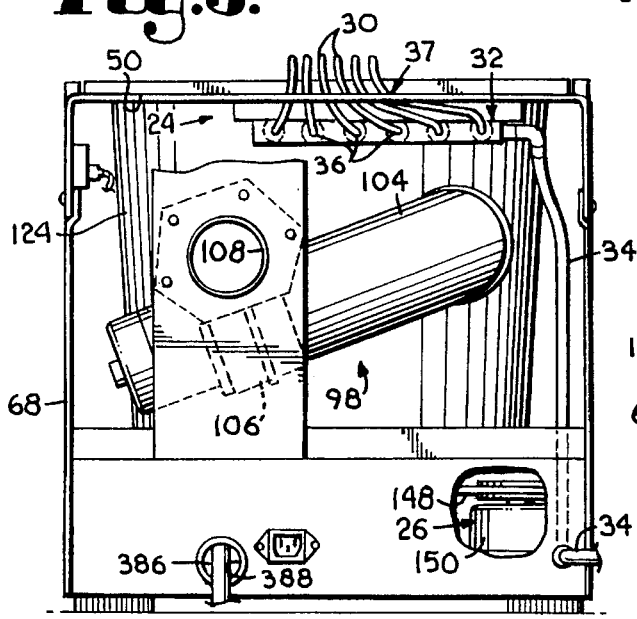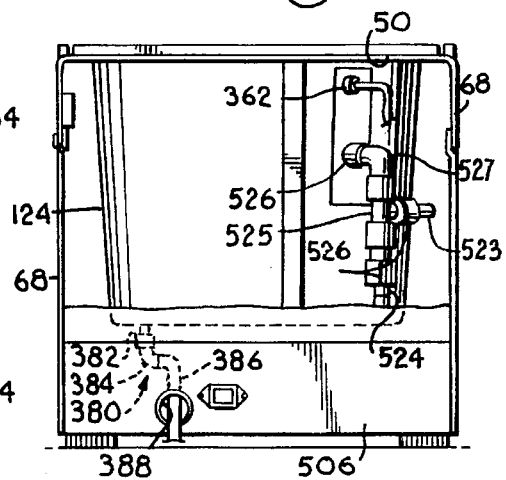

VORTEX EVAPORATION

This is a divisional of application Ser. No. 08/234,241 filed on Apr. 28, 1994, now U.S. Pat. No. 5,569,357.

FIELD OF THE INVENTION

This invention relates to vortex evaporators, and more particularly, to improvements for increasing the evaporation rate and for precisely controlling the operation of vortex evaporators.

BACKGROUND OF THE INVENTION

A vortex evaporator is a type of evaporator which moves one or more containers having a solvent and solid solution contained therein in an orbital motion to cause the solution to form a vortex configuration. The vortex increases the surface area of the solution which increases the evaporation rate of the solvent from the solid so that the solvent can be separated from the solid.

An example of such an evaporator is shown in U.S. Pat. No. 3,944,188 to Parker et al. The evaporator shown therein combines a vortexing motion, heat, and a vacuum to increase the evaporation rate of the solvent from the sol id. The vacuum is drawn by a vacuum pump that generates a controlled vacuum within the chamber of the vortex evaporator. The vacuum reduces the boiling point of the solvent and sol id solution, thereby permitting evaporation to occur at a lower temperature than would be possible under atmospheric conditions.

However, vacuum pumps require a vacuum trap to catch the evaporation vapors from the chamber of the vortex evaporator and a condenser to condense such vapors before they enter the pump. A significant limitation of vacuum pumps is that the valves are readily destroyed if excessive vapors overload the trap. Thus, vacuum evaporators are not cost effective at higher evaporation rates. Freezer traps can be employed to overcome this limitation. However, such traps are prohibitively expensive.

A further problem associated with prior art vortex evaporators is that the heaters for the evaporators were located outside of the evaporation chamber. The heat was transferred to the chamber via a transferable medium, such as an aluminum block, which formed part of the chamber wall. Such an arrangement was not very efficient because the heat was not directly supplied to the chamber of the vortex evaporator. Further, it was difficult to determine the temperature within the chamber because knowledge of the heater temperature did not provide an accurate measurement of the actual heat transferred to the chamber through the chamber wall. It would have certainly been more efficient to locate the heater within the chamber of the vortex evaporator to thereby directly supply heat to the chamber. However, the wires of the heater required a means of feeding the wires of the heater from the power supply located outside of the chamber to the heater within the chamber without affecting the vacuum. Known means of accomplishing that result were prohibitively expensive.

Yet another problem associated with prior art vortex evaporators is that a comprehensive and efficient control system has not been implemented to control operation of the vortex evaporator. Thus, accurate measurement of heat within the chamber was not directly measurable. Further, it would also be desirable to locate liquid level sensors within the chamber of the evaporator to determine the liquid or solvent level within each container. Such measurement devices required electrical connections from the control system located outside of the chamber to the sensors located within the chamber, and therefore suffer from the problem described above for heaters.

A further problem with prior art evaporators is that the rubber isolators used to smooth or dampen the orbital motion of the holder were only operable for a limited time. First, the rubber isolators are highly susceptible to many of the chemicals spilled or otherwise present in the chamber. Second, a metal plate at the top of the isolators frequently pulls out, rendering the isolators inoperable. Third, the use of isolators results in relatively high consumption of electrical power to provide the desired motion.

OBJECTS AND SUMMARY OF THE INVENTION

A primary object of the present invention is to provide a vortex evaporator capable of achieving higher evaporation rates than prior art vortex evaporators. Another similarly important objective is to provide a control system which optimizes performance of and control over the vortex evaporator. Thus, an object is to provide a vortex evaporator which provides faster evaporation rates than prior evaporators, and which also provides superior control over evaporation and separation of the solvent from the solid in the solution.

Another object of the present invention is to provide a vortex evaporator which achieves evaporation rates in excess of evaporation rates achieved by prior art vortex evaporators which utilize a vacuum. Thus, an object is to provide a vortex evaporator which does not require a vacuum, and therefore, is not limited to evaporation rates capable of being handled by costly, prior art vacuum evaporators. Specifically, an object is to provide a vortex evaporator which includes a means for blowing gas onto the liquid and solvent solution contained in the containers which are moved in an orbital motion at the same time by the vortex evaporator. More particularly, it is an object to blow an inert gas into each container to provide a pure source which lowers the partial pressure above the solution, and thus, increases the evaporation rate of the solution within each container. Another object is to combine vortexing motion, heat, and gas to obtain maximum evaporation rates. Yet another object is to drain off any electrical charge that might build up from the operation of the drive mechanism of the evaporator.

Another objective is to provide a cost effective and durable motion dampening assembly which overcomes the problems associated with prior art evaporators. The motion dampening assembly of the present invention provides a self-centering spring mechanism which dampens the orbital movement of the holder so that each container moves in the desired vortexing motion. More particularly, the present invention discloses a plurality of spring pairs, wherein each spring in the spring pair is coupled at one end to the container holder and coupled at the other end to the chamber.

Moreover, an object is to provide a vortex evaporator with a heater on the inside of the chamber to maximize the efficiency of the heater. Yet further objects are to provide a heat sensor and liquid level sensor within the chamber of the vortex evaporator to provide increased control over the operation and performance of the evaporator. To this end, an object is to provide a heat sensor within the chamber of the evaporator to directly measure the temperature imparted to the containers of solution, in contrast to the prior art method, which measured the heat supplied to the chamber from outside of the chamber of the evaporator. Yet another object is to connect the heat sensor to the control circuit for the evaporator to operate the heater in response to the temperature measured at the heat sensor. Similarly, an object is to provide a liquid level sensor within the chamber to determine the level of liquid remaining in the container. Additionally, an object is to connect the liquid level sensor to the control circuit for the evaporator to automatically turn off the vortex evaporator when the liquid level sensor senses a predetermined liquid level within the container. Another object is to provide a cost effective, airtight connection to the chamber for the control lines to the heat sensor and the liquid level sensor.

To accomplish these and related objects, a vortex evaporator is disclosed for evaporating liquid from a liquid and solid solution in a container. The vortex evaporator generally comprises a chamber, a container holder, a drive mechanism, a gas supply system and a control system. The chamber has a lid for providing selective access to the chamber. The holder is located inside the chamber and is adapted to hold at least one container. The drive mechanism is connected to the holder for moving the holder such that each of the containers will move in an orbital motion to cause the solution in the container to form a vortex configuration, thereby increasing the surface area of the solution. The gas supply system directs gas into the container to decrease the partial pressure on the solution, and thus to increase the evaporation rate of the liquid from the liquid and solid solution. The control system controls operation of the vortex evaporator, and particularly is connected to the drive mechanism and the gas system. In a preferred embodiment, the vortex evaporator further comprises a heater for heating the liquid and solid solution in the container. The heater is located within the chamber and is interfaced to the control system.

In a preferred embodiment, the vortex evaporator further comprises a heat sensor and at least one liquid level sensor and preferably one liquid level sensor corresponding to each container. The liquid level sensor is mounted within the chamber and senses the liquid level in the corresponding container. The heat sensor is also mounted within the chamber and senses the temperature within the chamber.

In an alternative embodiment, the gas supply system is replaced with a vacuum. In this embodiment, the liquid level sensor and the heat sensor may control operation of the vortex evaporator in the manner described above. In either embodiment, the vortex evaporator may comprise a means for dampening the motion of the holder. A motion dampening assembly comprises a plurality of pairs of springs and provides the desired vortexing motion. Further, the vortex evaporator may comprise means for dissipating the charge that may build up in the chamber in response to the operation of the drive mechanism. More specifically, a ground plane is etched onto a fiberglass plate to drain off the charge from the drive mechanism.

Thus, the vortex evaporator of the present invention provides evaporation rates superior to prior art evaporators. Moreover, the location of the heater within the chamber of the evaporator in conjunction with the heat sensor and the liquid level sensor provides sophisticated control of the evaporation rate, as well as the operation of the vortex evaporator generally. Further, a vacuum feed thru fitting provides an airtight seal for interfacing the heat sensor and the liquid level sensor to the control system.

BRIEF DESCRIPTION OF THE DRAWINGS

In the accompanying drawings which form a part of the specification and are to be read in conjunction therewith and in which like reference numerals are used to indicate like parts in the various views:

FIG. 1 is a perspective view of a vortex evaporator constructed according to a preferred embodiment of the present invention;

FIG. 2 is a top plan view of the vortex evaporator shown in FIG. 1;

FIG. 3 is a fragmentary bottom view taken generally along the plane of line 3—3 of FIG. 4 in the direction of the arrows, showing an enlarged view of the gas feed tubes secured to the underside of the lid of the vortex evaporator;

FIG. 4 is a fragmentary side elevation view taken generally along the plane of line 4—4 of FIG. 3 in the direction of the arrows, showing a bracket securing the gas feed tubes to the underneath side of the lid of the vortex evaporator;

FIG. 5 is a rear elevation view of the back of the vortex evaporator;

FIG. 8 is a rear elevation view of an alternative embodiment of the vortex evaporator which applies a vacuum to the evaporation chamber;

DESCRIPTION OF THE PREFERRED EMBODIMENT

Figure 6:
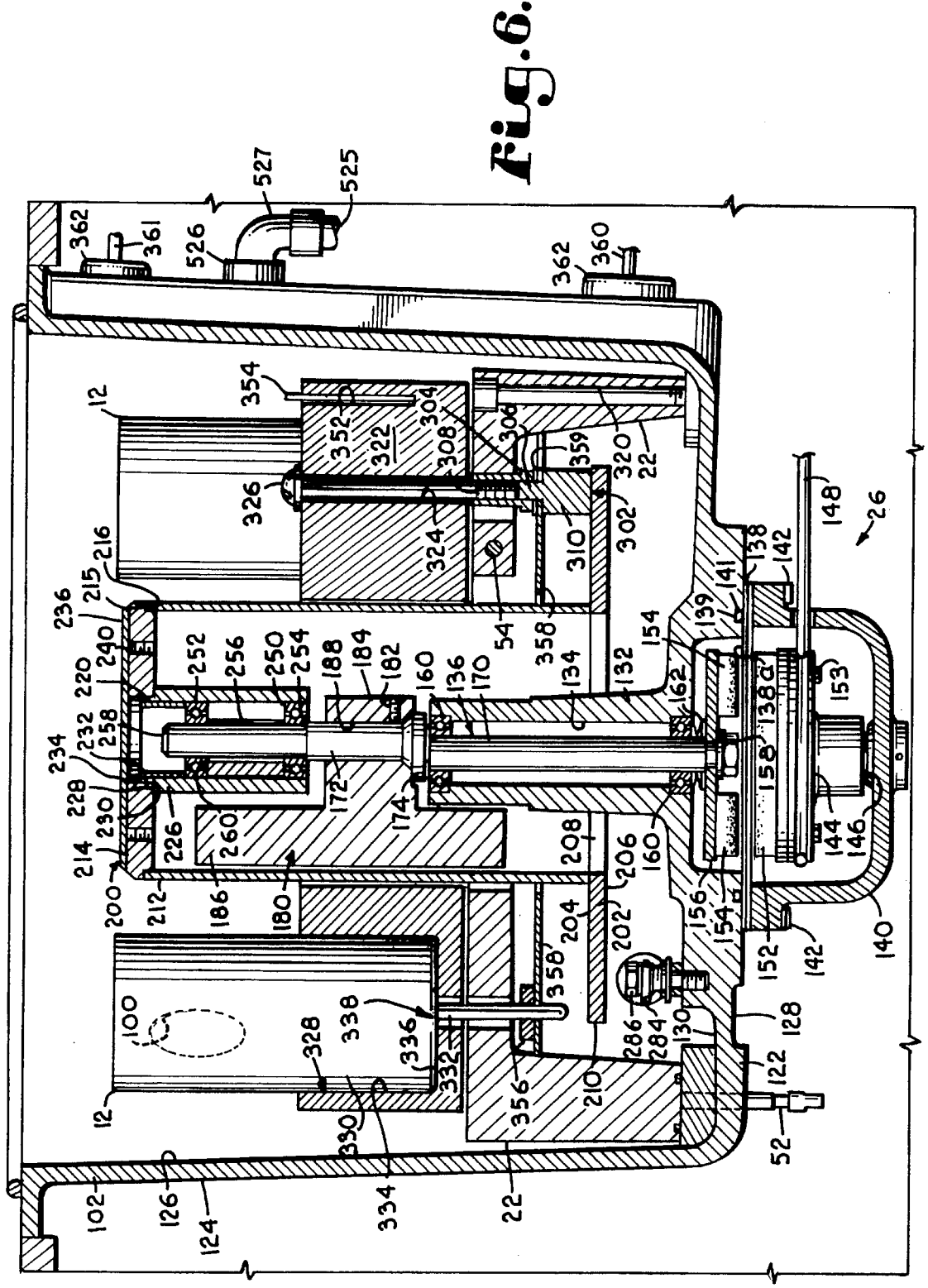
FIG. 6 is a fragmentary side cross-sectional view taken generally along the plane of line 6—6 of FIG. 2 in the direction of the arrows, showing the internal structure of the vortex evaporator.

Referring to the figures, a vortex evaporator constructed according to a preferred embodiment of the present invention is shown in FIG. 1 and is designated generally by the numeral 10. The vortex evaporator is adapted to hold at least one container 12, and preferably a plurality of such containers. The device 10 accomplishes rapid evaporation of liquid from a liquid and solid solution (not shown) within the containers. The vortex evaporator 10 according to this embodiment generally comprises a chamber 14, a housing 16, a control panel 18, a lid 20, a heater 22 (shown in FIG. 6), a gas supply system 24, and a drive mechanism 26 (shown in FIG. 6) for providing a vortexing motion. The vortex evaporator further comprises a control system 28 (shown in FIG. 11) for controlling operation of the heater 22, the gas supply system 24 and the drive mechanism 26.

The terms "orbital motion" and "vortexing motion" are used herein to describe generally the movement of an individual container with respect to a vertical axis through the center of that container. As a result of the orbital or vortexing motion of the container, the solution inside the container forms a vortex configuration. In the preferred embodiment of the present invention, the holder does not actually orbit the shaft.

The gas supply system 24 comprises gas feed tubes 30 which connect to a manifold 32 (shown in FIG. 5). A gas supply tube 34 connects between a gas source (not shown) and the manifold 32. The gas source supplies gas to the manifold 32 through gas supply tube 34. The manifold 32 includes solenoids 36 which cause the gas supplied to the manifold 32 to be evenly distributed and supplied to the gas feed tubes 30, as is well known in the art. As shown in FIGS. 1 and 5, the gas feed tubes 30 extend from the manifold 32 through holes 37 over the back of the vortex evaporator 10 and through corresponding holes 40 in the lid 20. Referring to FIGS. 1–4, six gas feed tubes 30 are shown. The gas feed tubes are connected to the bottom surface 50 of lid 20. In a preferred embodiment, the tubes 30 are flexible plastic tubes where outside the lid, but tubes 30 are stainless steel tubes where passing through lid 20 and extending into the chamber 14.

Referring to FIG. 4, a main bracket 56 is secured to the lid 20 by screws 58. The bracket comprises an upper surface 60 for securing against the bottom surface 50 of lid 20. The upper surface 60 of main bracket 56 comprises notches 62 sized to snugly receive the gas feed tubes 30. The notches 62 are generally rectangular in cross-section, and the bracket 56 comprises a notch 62 for each gas feed tube 30. The main bracket 56 maintains the gas feed tubes 30 in fixed, spaced apart relation. Referring to FIG. 3, a secondary bracket 80 is secured to the tubes 30 to further secure the tubes 30 in place. The secondary bracket 80 is secured to the lid 20 by known means such as screws 82.

The gas feed tubes 30 extend from main bracket 56 toward the front edge 64 of lid 20 to bends 66, which are generally horizontal, ninety degree bends. The gas feed tubes extend from the bends 66 towards the sides 68 of lid 20. Referring to FIG. 1, each of the gas feed tubes 30 comprise second bends 70 which direct the gas feed tubes 30 generally perpendicularly downward into the chamber 14. The gas feed tubes are spaced generally evenly within the chamber 14 so that each tube 30 is adapted to extend downwardly into a corresponding container 12. As shown in FIGS. 1–5, the vortex evaporator 10 preferably comprises six gas feed tubes 30, and thus is adapted to direct gas into six containers 12 simultaneously. However, the number of tubes and containers may be varied to accommodate different applications.

The gas source preferably comprises an inert gas source for supplying purified gas across the solution contained within the containers 12 to prevent contamination of the solutions. Use of an inert gas increases the evaporation rate of the solution by lowering the partial pressure above the solution as a result of the dry gas absorbing vapor in the immediate area of the surface of the solution. Nitrogen is one inert gas which can be used in this application, and nitrogen is desirable because of its low cost. Alternatively, other inert gases could be employed.

Referring to FIG. 5, the vortex evaporator 10 also comprises a ventilation system 98 for venting the gas (e.g., nitrogen) and the evaporated solution fumes from the chamber 14. The ventilation system 98 comprises a hole 100 (shown in FIGS. 1 and 6) formed in the annular chamber wall 102. A ventilation tube 104 is matingly secured to an outer surface 124 of chamber wall 102 concentrically adjacent to the perimeter of hole 100. The ventilation tube 104 is coupled with a blower 106 which draws fumes from the chamber 14 through hole 100 and ventilation tube 104 and exhausts the fumes through outlet 108. The blower 106 is well known in the art, and therefore will not be described further herein.

Referring next to FIG. 6, the chamber 14 comprises annular side wall 102 and a bottom wall 122 which is preferably formed integrally with the annular side wall 102.

The annular side wall 102 comprises outer surface 124 and an inner surface 126, both of which extend upwardly and slightly outwardly from the bottom wall 122. The bottom wall 122 likewise comprises an outer surface 128 and an inner surface 130. The bottom wall 122 also comprises an upwardly extending sleeve 132, formed integrally therewith. The sleeve 132 has a cylindrical hole 134 for receiving an eccentric shaft 136, as will be described in further detail below.

A plate 138 is secured to the outer surface 128 of bottom wall 122 by bolts 142. An O-ring 139 is received within an annular groove 141 and provides an airtight seal between the plate 138 and the bottom wall 122 of the chamber 14. A bracket 140 is secured to the plate 138. The bolts 142 secure both the bracket 140 and the plate 138 to the bottom wall 122 of chamber 14. A pulley 144 is rotatably mounted about a generally vertical axis to bracket 140 by a bearing assembly 146. A drive belt 148 secures to the pulley 144, and also secures to a motor 150 (shown in FIG. 5). A magnet 152 is mounted to the top of pulley 144 and below plate 138 by bolts 153. Motor 150 drives belt 148 which causes pulley 144 to rotate, and thus causes magnet 152 to rotate. The rotation of magnet 152 causes annular magnet 154 to rotate. Magnet 154 is secured to a plate 156. Plate 156, and thus magnet 154, are mounted to the eccentric shaft 136 by nut 158.

The plate 138 which separates the magnets 152 and 154 is preferably fiberglass with a conductive grid surface etched on one side. This allows the magnetic waves to permeate the plate, to provide an airtight seal to the chamber 14, and to prevent heat build up when the magnets rotate. The conductive surface, designated 138a in FIG. 6, is exposed and thus forms a ground plane. Any charge that might result from the movement of the drive mechanism will be discharged since the surface 138a is grounded to the chamber 14 by way of bolts 142. In a preferred embodiment, plate 138 comprises a printed circuit (PC) board with a conductive grid.

The eccentric shaft 136 rotates as magnet 154 rotates. Bearing assemblies 160 are mounted to the sleeve 132 of bottom wall 122 between the sleeve and the eccentric shaft 136. The bearing assemblies 160 facilitate rotation of the eccentric shaft 136 within sleeve 132. Further, four spring washers 162 are located about eccentric shaft 136 between bearing assemblies 160 and plate 156 to preload the shaft within the bearings and to take up clearances.

The eccentric shaft 136 comprises a bottom shaft portion 170 and an upper shaft portion 172 which are joined together by disc 174. As shown in FIG. 6, the lower shaft portion 170 is offset from the upper shaft portion 172. A counterweight 180 is secured to the upper shaft portion 172 of eccentric shaft 136 by set screw 182 which is adapted to contact a flat surface (not shown) on the eccentric shaft 136. The counterweight 180 comprises an annular collar 184 and an arcuate portion 186. The collar 184 has a hole 188 sized to receive the upper shaft portion 172 of eccentric shaft 136. The counterweight balances the eccentric motion of the eccentric shaft.

The counterweight 180 and eccentric shaft 136 are covered by a housing 200, which is secured to the bottom wall 122 of chamber 14, as will be described below. The housing 200 comprises an annular ring 202 having a top surface 204, a bottom surface 206, an inner surface 208, and an outer surface 210. The housing 200 further comprises a generally cylindrical wall 212 and an annular cover 214. Cylindrical wall 212 is secured to the upper surface 204 of annular ring 202 adjacent the inner surface 208 of the annular ring. Cover 214 has an annular step portion 216 adapted to mate with and secure to the annular corner 215 of cylindrical wall 212. The cover 214 further comprises a hole 220 which is generally circular and located at the center of cover 214 to provide access to the eccentric shaft 136.

The housing 200 further comprises an annular sleeve 226. The annular sleeve 226 has an annular stepped portion 228 which is adapted to mate with the annular corner 230 of cover 214. The annular sleeve 226 further comprises an annular shoulder extension 232 having a top surface 234 which forms an annular ridge. The cover 214 further comprises threaded holes 240 which are adapted to receive a tool (not shown) which is adapted to thread into the holes 240 to remove housing 200 to provide access to the eccentric shaft 136. A generally circular plate 236 is coupled to the top of cover 214. Plate 236 covers holes 220 and 240.

Bearing assemblies 250 and 252 are secured to the annular sleeve 226 by known means, such as by adhesive. The upper shaft portion 172 of eccentric shaft 136 has a stepped portion 254. The bearing assembly 250 rests upon and is partially supported by the stepped portion 254. An annular spacer 256 is sized to slide over the top 258 of upper shaft portion 172 and rests upon the top of bearing assembly 250. The bottom of bearing assembly 252 rests upon the top surface 260 of annular spacer 256, thereby partially supporting the bearing assembly 252 and maintaining the bearing assemblies 250 and 252 in spaced relation.

Figure 7:
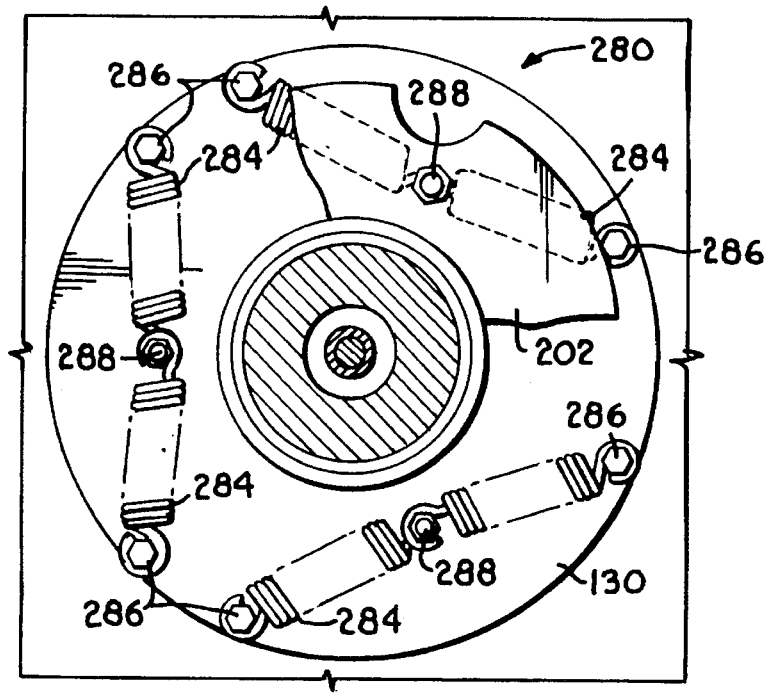
FIG. 7 is a fragmentary top plan view showing the motion dampening assembly of the vortex evaporator.

The annular ring 202 is coupled to the inner surface 130 of bottom wall 122 of chamber 14 by a motion dampening assembly 280. Referring to FIG. 7, the dampening means 280 comprises six springs 284 each of which comprises two ends. One end of each of the springs 284 is secured to one of a plurality of bolts 286, and thus to the bottom wall 122 of chamber 14. Also, as shown in FIG. 7, the six springs 284 are arranged in three pairs of two adjacent springs in the preferred embodiment. Three bolt and nut combinations 288 interconnect the free ends of adjacent springs and are also secured to the bottom of annular ring 202. Thus, the springs 284 couple the annular ring 202 with the bolts 286 which are secured to the bottom wall 122 of chamber 14. When eccentric shaft 136 rotates, it imparts an orbital motion to the housing 200, which motion is dampened and smoothed by the springs 284. Alternatively, one of ordinary skill in the art could modify the dampening means 280 by securing nut and bolt combinations 288 to the chamber 14 and securing bolts 286 to ring 202. As will be described immediately below, the containers 12 and container holder 322 are coupled to and move with the housing 200.

Turning back to FIG. 6, a container holder 322 is secured to the upper surface 204 of annular ring 202 of housing 200 by a hex assembly 302. The hex assembly 302 comprises an annular top hex section 304 having an outer surface adapted to mate with a hex wrench and an inner surface that defines a threaded hole 308. The lower portion 310 has a generally smooth, circular outer surface and a protrusion 306 preferably formed integrally therewith. The lower portion 310 secures to the upper surface 204 of annular ring 202 by known means such as by welding. The top hex section 304 is coupled to the lower portion 310 by securing the top hex section 304 to protrusion 306 of lower portion 310.

Figure 9:
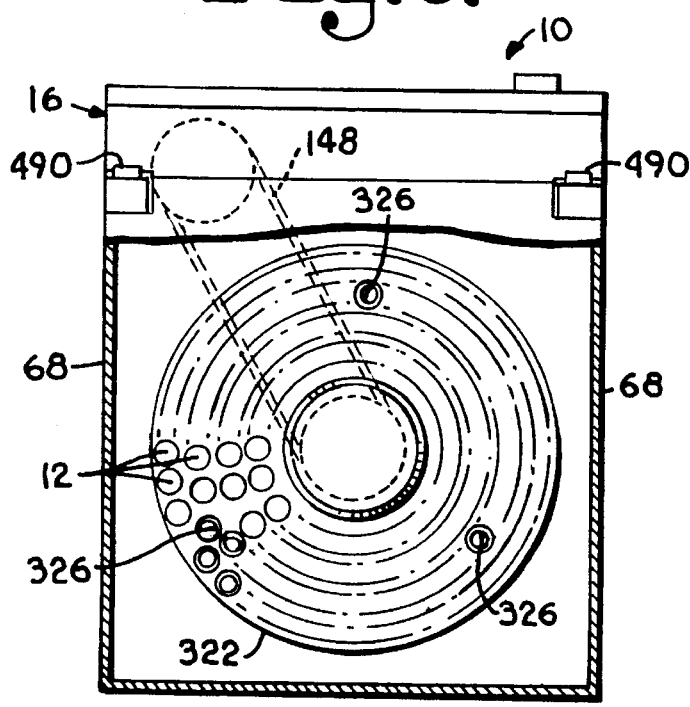
FIG. 9 is a top plan view of the vortex evaporator showing the vials secured within the chamber.

The container holder 322 has a hole 324 that is aligned with hole 308 and adapted to receive a bolt 326 for securing the container holder 322 to the hex assembly 302 (also shown in FIG. 9). In a preferred embodiment, the container holder 322 includes at least three corresponding holes 324 for receiving three bolts 326, as described above. The bolts 326 rigidly secure the container holder 322 to the hex assemblies 302 and thus to housing 200.

The container holder 322 presents a plurality of cylindrical recesses 328 for snugly receiving the containers 12. The container holder 322 (shown in FIG. 6) preferably comprises six cylindrical recesses 328. The cylindrical recesses 328 should be spaced equidistant apart around the perimeter of the container holder 322.

The container 12 (left-hand side of FIG. 6) comprises an upper container portion 330 and a stem 332 which is in fluid communication with the upper container portion 330. The cylindrical recesses 328 of holder 322 are formed by a cylindrical side wall 334 and a generally circular bottom 336. The circular bottom 336 has a hole 338 through which stem 332 is received. Recess 328 is designed to hold containers with or without a stem, but the liquid level sensor of the present invention is not designed to detect the liquid level in a container without a stem.

The heater 22 is coupled to the bottom of the chamber 14 by a bolt (not shown) secured in a recess 320 (right-hand side of FIG. 6) formed in the generally U-shaped annular heater block. Heater 22 is preferably a cast aluminum resistance heater. In a preferred embodiment, a plurality of bolts are secured in a plurality of locations so that heater 22 remains stationary within the chamber 14 as container holder 322 moves in an orbital motion. The heater 22 underlies container holder 322 and transfers heat to the container holder 322 and thus to the containers 12. Also, the container holder 322 includes a recess 352 for receiving a heat sensor 354 which is secured within the recess 352. The heat sensor 354 is preferably stainless steel. The heat sensor 354 is electrically coupled to the control system 28 to automatically control the temperature within the chamber 14.

Additionally, a liquid level sensor 356 (FIG. 6) rests on a PC board 358 that is secured between the top section 304 and the lower portion 310 of hex assembly 302. One or more shims 359 may also be secured between each top hex section 304 and lower portion 310 to maintain or adjust the gap between the top surface of heater 22 and the bottom surface of container holder 322. In a preferred embodiment, the gap is maintained from approximately 0.045" to 0.050" and allows the heater 22 to remain stationary. Alternatively, the heater 22 may be coupled to holder 322 rather than chamber 14 so that heater 22 is not stationary.

The liquid level sensor 356 comprises a light emitting diode (LED) and light receiving means, which are well-known in the art. Sensor 356 and board 358 present a hole (not shown) for receiving the stem 332 of each container 12. The refraction of the light through the stem 332 of container 12 provides an electrical signal which indicates whether liquid is contained in the stem 332. If the liquid level sensor 356 detects that the solution level within the stem has fallen below the level of the sensor, the sensor transmits a signal to the control system 28 of evaporator 10 so that the control system can automatically turn off the evaporator, as will be described further below. The vortex evaporator preferably includes a liquid level sensor 356 for each container 12. While only one liquid level sensor might be used, it is preferable to provide one liquid level sensor for each container to provide accurate control and sensing for each container. If only one sensor is used for a plurality of containers, it is possible that the solution level in all containers will not reach the same predetermined shutdown level at the same time.

The liquid level sensor 356 and heat sensor 354 both require electrical connections to control system 28 which must feed through the chamber side wall 102. The electrical connections include wire 360 for liquid level sensor 356 and wire 361 for heat sensor 354. Although depicted as single wires in FIG. 6, wires 360 and 361 may actually represent a plurality of control leads. Wires 360 and 361 feed through the chamber side wall 102 through their respective vacuum feed thru fittings 362, as shown in FIG. 6. Wires 360 and 361 pass through a hole (not shown) bored in each fitting 362. This hole may be filled with a potting compound such as epoxy or another hardenable resinous material to provide an airtight seal. In a preferred embodiment, a potting compound may also surround heat sensor 354.

The heater 22 includes a tubular heater element 52 (left-hand side of FIG. 6) that feeds through bottom wall 122 and into heater 22. The opening in wall 122 where element 52 enters chamber 14 is sealed, such as by an O-ring or a potting compound, to provide an airtight connection. Element 52 loops around a passageway 54 so as to provide heat in a substantially uniform manner throughout heater 22. In a preferred embodiment, element 52 makes one loop within the inner portion of the heater 22 and one loop within the outer portion of heater 22. A portion of the passageway 54 is shown in cross-section (right-hand side of FIG. 6) on the inner portion of heater 22. Element 52 is connected to the control system 28 so that heater 22 may be regulated in response to heat sensor 354.

The vortex evaporator 10 also comprises a drain assembly 380 (shown in FIGS. 5 and 8) for draining evaporated liquids or spilled liquids within the chamber 14. The drain assembly 380 includes a fitting 382 under the bottom wall 122 of chamber 14 which is adapted to mate with an elbow 384 connected to a drain tube 386. The tube 386, which feeds through a hole 388 in the back of the vortex evaporator, is preferably stainless steel. Tube 386 may also be utilized for other purposes, as will be described below with respect to FIG. 8.

Referring to FIG. 1, the control panel 18 provides a plurality of controls for controlling and operating the vortex evaporator 10. The control panel 18 comprises a plurality of buttons which are coupled to the control system 28. Button 450 is an on/off switch which turns power on and off to the vortex evaporator 10. An indicator lamp, such as incandescent bulb 452, illuminates when the vortex evaporator 10 is activated by button 450.

Button 454 is a dry switch, which causes the vortex evaporator 10 to continue operating (i.e., evaporating solution) for a designated time after the liquid level sensors 356 detect that the solution in the stem 332 of one of the containers 12 is below a predetermined level. When the dry switch is not activated, the liquid level sensors 356 "alert" the control system 28 to automatically turn off the vortex evaporator 10 upon detecting that the liquid level within a stem of one of the containers 12 has evaporated below a predetermined level. The dry switch 454 causes the vortex evaporator to evaporate the remaining liquid away from the solid in the solution so that only the solid remains. While this is desirable for some applications, it is desirable in other applications to have the solid immersed in a small amount of liquid remaining in the stem 332 of container 12.

As stated above, the container holder 322 can accommodate up to six containers. Buttons 456, 457, 458, 459, 460, and 461 correspond to each of the six containers 12, respectively. Depressing one of the buttons 456–461 causes gas flow through the corresponding gas feed tube 30 to be enabled or disabled, and likewise causes the corresponding liquid level sensor 356 corresponding to the particular container 12 to be enabled or disabled. For example, if buttons 456, 457, and 458 are enabled, the corresponding gas feed tubes 30 and corresponding liquid level sensors 356 will be activated only for the containers 12 corresponding to those buttons. On the other hand, the gas feed tubes 30 and liquid level sensors 356 for the containers 12 corresponding to buttons 459–461 will be deactivated by the control system 28.

Button 464 enables or disables the motor 150 which drives the eccentric shaft 136, and thus enables or disables the vortexing motion applied to the containers 12. If button 464 is activated when a run/stop switch 465 is activated, the vortex evaporator will immediately begin applying a vortexing motion to the containers 12 on the container holder 322.

Button 465 is a run/stop switch which, when activated to the run mode, initiates all functions that have been enabled. When switch 465 is in the stop mode, all selected functions are disabled, which stops operation of the vortex evaporator 10 without shutting off power to the evaporator by button 450.

Button 466 is a heat switch which enables or disables the heater 22. Button 468 is a timer switch which enables or disables a preset timed automatic shutdown. If a time is entered, as will be described below, it will override the liquid level sensors and cause automatic shutdown after the preselected time elapses, irrespective of whether solution remains in the container 12. In fact, the timer switch would be the primary shutdown mechanism in an embodiment of the present invention that does not include any liquid level sensors or when containers without stems are used. Each of the buttons 454–461, 464–466, and 468 has an LED indicator light 470 which indicates whether the button is activated.

The control panel 18 further comprises a display 472 for displaying parameters relating to the operation of the vortex evaporator 10. LEDs 474, 475, 476, 477, and 478 indicate which functional parameter is displayed on the display 472. LED 474 indicates that the timing parameter is displayed. LED 475 indicates that the vortex speed parameter is displayed. LED 476 indicates that the set temperature parameter is displayed. LED 477 indicates that the actual temperature as sensed by the heat sensors 354 is displayed. LED 478 indicates the end point. Button 480 is a display button which when depressed sequentially alternates between the functional parameters corresponding to LEDs 474–478.

Button 482 allows a parameter to be increased, and button 484 allows a parameter to be decreased. Depressing either button 482 or 484 causes the functional parameter on display 472 to increase or decrease, respectively, and thus allows for accurate adjustment of the parameters for controlling operation of the vortex evaporator 10. For example, to adjust the desired temperature for the chamber 14, the user would depress the display button 480 until the LED 476 illuminates, which corresponds to the desired temperature of the chamber. The display 472 would then display the parameter corresponding to the previous desired temperature. To change that temperature, the increase and decrease buttons 482 and 484, respectively, could be depressed to alter the desired temperature of the chamber 14.

Figure 11:
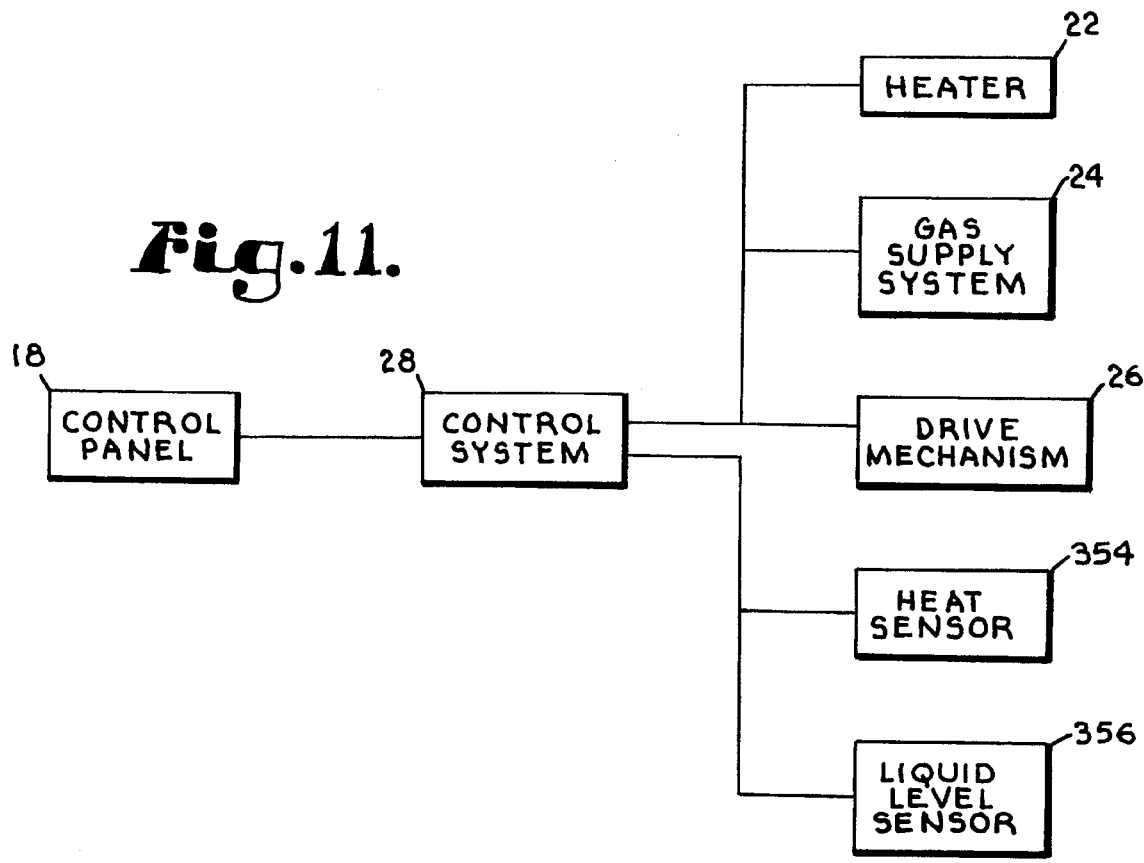
FIG. 11 is a block diagram of the interconnection of the control system for the vortex evaporator.

Referring to FIG. 11, the above described buttons of the control panel 18 are interfaced to the control system 28. The control system 28 responds to commands entered at the control panel 18, and automatically controls operation of the vortex evaporator. As shown, the control system may be interfaced to the heater 22, the gas supply system 24, the drive mechanism 26, the heat sensor 354, and the liquid level sensors 356 to control the operation of those devices. The control system can comprise any commercially available microprocessor and software programming to effect the logical steps described herein. In a preferred embodiment, control system 28 comprises a PC board and a microprocessor located behind the display panel 18. Of course, the control system 28 could also be a hardwired device using electronic or electrical components to perform the functions of the software.

Referring to FIGS. 1 and 2, the lid 20 is attached to the housing 16 of the vortex evaporator by hinges 490 which accommodate movement of the lid between an open position in which the chamber 14 can be accessed and a closed position in which the chamber is closed. Slots 492 are formed in the lid so that air can be drawn by the blower through the slots. Alternatively, slots or recesses could be formed in a rubber gasket that is positioned between the top of the chamber and the bottom of the lid.

Alternative Embodiment

Referring to FIGS. 5–10 and initially to FIG. 8, in an alternative embodiment, the gas supply system 24 is replaced with a vacuum system. The vacuum system comprises a vacuum pump (not shown) which applies a vacuum to the chamber 14 through tube 386. The term "vacuum" is used herein to mean a reduction in pressure within the chamber relative to atmospheric pressure; "vacuum" does not refer to an absolute vacuum.

The tube 386 is coupled to the fitting 382 of the drain assembly 380. The tube 386 extends from the elbow 384 through the outlet 388 in the back plate 506. In this alternative embodiment, the portion of tube 386 extending through outlet 388 is connected to a vacuum system (not shown) which comprises a vacuum pump to draw the vacuum and may comprise a vacuum trap to trap vapors from the chamber 14. In a preferred embodiment, either a rotary vane or a diaphragm pump may be used. A rotary vane vacuum pump includes a vacuum trap, but a diaphragm vacuum pump does not. Vacuum pumps and traps are well known in the art and will not be described further herein.

Figure 10:
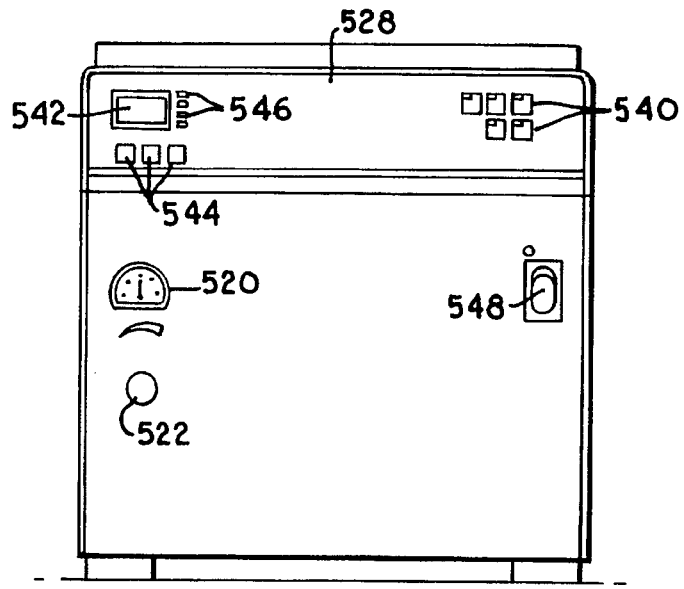
FIG. 10 is a front elevation view showing the control panel for an alternative embodiment of the vortex evaporator.

Referring to FIGS. 8 and 10, the vacuum system also comprises a vacuum gauge 520 and a bleeder valve 522. A tube 523 couples between the chamber 14 and the vacuum gauge 520 to provide an accurate measurement of the vacuum within the chamber 14. A tube 524 couples between the chamber 14 and the bleeder valve 522 which can be used to manually reduce the vacuum level within the chamber as is well known in the art. The tubes 523 and 524 are coupled to the chamber 14 by a T-connector 525 and corresponding fittings 526 and elbow 527.

The vacuum pump can be controlled to apply a desired vacuum level to the chamber 14. In the preferred embodiment, the vacuum pump is connected to control system 28 in place of the gas supply system 24 as shown in FIG. 11. The control system 28 can be activated by a control panel 528 (shown in FIG. 10) to automatically control the vacuum level within the chamber The control panel 528 for this embodiment comprises a plurality of buttons 540 for controlling operation of the vortex evaporator. The buttons 540 are similar to the buttons of the control panel 18 shown in FIG. 1, except that buttons are not necessary for the gas supply system, but a button is necessary for activating the vacuum system. Further, the control panel 528 comprises a display panel 542, buttons 544 and indicators 546 which work in conjunction with the display as described above for the control panel 18. Also, the control panel comprises an on/off switch 548 for connecting and disconnecting power to and from the vortex evaporator, respectively.

It should also be understood that the slots 492 in the lid 20 are not included in this alternative embodiment. The lid 20 must form an airtight seal for the chamber 14 to allow the vacuum pump to draw a vacuum within the chamber 14. Also, referring to FIG. 6, the hole 100 should only be included in the wall 102 of the chamber 14 for the "gas supply system embodiment" and not for the "vacuum system embodiment." The inclusion of the hole 100 in FIG. 6 is intended only to show that the drive mechanism 26, heater 22, heat sensor 354, and liquid level sensors 356 may be identical for either embodiment.

Further, for the vacuum embodiment, the container holder 322 may include a plurality of recesses 328 to hold a multiplicity of containers 12, as shown in FIG. 9. For the "gas supply system embodiment," the vortex evaporator 10 may include six gas feed tubes 30 for increasing the evaporation rate of the solution contained in at least six containers 12. However, the number of gas feed tubes 30 could be varied depending on the needs of the particular system.

Operation

For either embodiment, the user must begin by placing at least one container 12, having solution therein, into a recess 328 of the container holder 322 within chamber 14. Typically, a plurality of containers 12 will be placed in a plurality of recesses 328 of the container holder 322.

After the containers are placed in the container holder 322, the user must decide which factors will be applied to the solution to evaporate the liquid from the liquid/solid solution. For either embodiment, the buttons of either control panel 18 or 528 can be activated to selectively control operation of the heater 22, the drive mechanism 26, and either the gas supply system 24 or the vacuum system, depending on the embodiment. For example, in the "gas supply system embodiment," the speed of the vortex can be selected, the temperature within the chamber 14 can be selected, and gas can be supplied onto solution contained within any one of six containers 12. Further., these factors (gas, heat, and vortex) can be applied individually, or in any combination, as selected by the user. However, the maximum evaporation rate is achieved by combining each of the factors. The display 472 allows the user to monitor the status of variables within the chamber, such as the temperature.

Likewise, in the "vacuum system embodiment," the factors of vortex, heat, and vacuum can be selectively activated and controlled to evaporate solution within a multiplicity of containers 12 through the use of buttons 544 of control panel 528 (shown in FIG. 11). The display 542 allows the user to monitor the status of variables within the chamber, such as the vortex speed or temperature.

In both embodiments, the heat sensor 354 and the liquid level sensors 356 provide enhanced control over the operation of the vortex evaporator 10. The heat sensor 354 provides accurate feedback of the temperature within the chamber 14 and provides signals to the control system 28 to allow the control system to accurately control the temperature within the chamber 14. Similarly, the liquid level sensors 356 accurately determine when the liquid level in a particular container falls below a predetermined level. The corresponding liquid level sensor 356 transmits a signal to the control system which causes the control system 28 to turn the vortex evaporator off so that the particular container 12 can be removed. Thereafter, the vortex evaporator can be reactivated until another container 12 drops below the predetermined level, at which time the corresponding liquid level sensor will automatically cause the vortex evaporator to turn off again. This procedure can be repeated until the solution level in each of the containers drops below the predetermined level. Thus, the liquid level sensors 356, as well as the heat sensor 354, allow the vortex evaporator to precisely control the evaporation of solution within the containers 12.

It should be noted that vacuum feed thru fittings 362 allow the electrical connections for the heat sensor 354 and the liquid level sensors 356 to be fed through the wall 102 of the chamber 14. The fitting for heat sensor 354 is located above the fitting for liquid level sensor 356 as shown in FIG. 6. However, the presence of fittings 362 and the sensors 354 and 356 are not dependent upon one another. For example, in an embodiment of the present invention that does not include liquid level sensors 356 and lower fitting 362, heat sensor 354 and upper fitting 362 may still be present as shown in FIG. 6 and as previously described.

Electrical power is supplied to the various components of the present invention in a manner well-known in the art. In a preferred embodiment, a 115 volt alternating current (AC) power supply is coupled to the components outside the chamber.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, we claim:

1. A method of evaporating liquid from a liquid and solid solution in a container, said method comprising:

providing a vortex evaporator comprising a chamber and a container holder inside the chamber;

moving the container holder in an orbital motion such that the solution forms a vortex configuration within the container to increase the surface area of the solution and promote liquid evaporation;

directing gas into the container from a point source overlying the solution to decrease the partial pressure on the solution thereby increasing the evaporation rate of the liquid from the solution; and controlling the motion of the container holder.

2. The method of claim 1, further comprising applying heat to the container to increase the evaporation rate of the liquid from the solution.

3. The method of claim 2, further comprising sensing the temperature within the chamber.

4. The method of claim 3, further comprising controlling the application of heat to the container in response to the temperature sensed within the chamber.

5. The method of claim 1, further comprising dampening the orbital motion of the container holder.

6. The method of claim 1, further comprising sensing a predetermined liquid level in the container from within the chamber.

7. The method of claim 6, further comprising turning off the vortex evaporator upon detecting the predetermined liquid level within the container.

8. The method of claim 1, further comprising providing a plate having a ground plane for draining an electrical charge caused by the orbital motion of the container holder.

9. A method of evaporating liquid from a liquid and solid solution in a container, said method comprising:

providing a vortex evaporator comprising a chamber and a container holder inside the chamber;

moving the container holder in an orbital motion such that the solution forms a vortex configuration within the container to increase the surface area of the solution and promote liquid evaporation;

drawing a vacuum within the chamber to decrease the boiling temperature of the solution without moving liquid from the container into the chamber;

controlling the motion of the container holder providing a heater inside the chamber;

heating the container holder to increase the temperature of the solution in the container; and controlling the operation of the heater.

10. The method of claim 9, further comprising dampening the orbital motion of the container holder.

11. The method of claim 9, further comprising sensing the temperature within the chamber.

12. The method of claim 11, wherein the operation of the heater is controlled in response to the temperature sensed within the chamber.

13. The method of claim 9, further comprising sensing a predetermined liquid level in the container from within the chamber.

14. The method of claim 13, further comprising turning off the vortex evaporator upon detecting the predetermined liquid level within the container.

15. The method of claim 9, further comprising providing a plate having a ground plane for draining an electrical charge caused by the orbital motion of the container holder.

\* \* \* \* \*